United States Patent [19]

Allen et al.

[11] Patent Number: 4,490,300

[45] Date of Patent: Dec. 25, 1984

[54] LIQUID DIPHENYLMETHANE DIISOCYANATE COMPOSITIONS

[75] Inventors: Gary F. Allen; Richard S. Pantone, both of New Martinsville, W. Va.

[73] Assignee: Mobay Chemical Corporation, Pittsburgh, Pa.

[21] Appl. No.: 538,054

[22] Filed: Sep. 30, 1983

[51] Int. Cl.³ .................. C07C 69/00; C07C 125/06
[52] U.S. Cl. .................. 260/453 SP; 260/453 AM; 560/27; 560/26; 521/155; 521/159
[58] Field of Search .......... 260/453 SP, 453 AM; 560/26, 27

[56] References Cited

U.S. PATENT DOCUMENTS

| | | | |
|---|---|---|---|
| 3,152,162 | 10/1964 | Fischer et al. | 260/453 |
| 3,384,653 | 5/1968 | Erner et al. | 260/453 |
| 3,394,165 | 7/1968 | McClellan et al. | 260/453 |
| 3,449,256 | 6/1969 | Farrissey et al. | 252/182 |
| 3,640,966 | 2/1972 | Hennig et al. | 260/77.5 R |
| 3,641,093 | 2/1972 | Brooks et al. | 260/453 AR |
| 3,644,457 | 2/1972 | König et al. | 260/453 SP |
| 3,674,828 | 7/1972 | Brooks et al. | 260/453 P |
| 3,701,796 | 10/1972 | Saaty et al. | 260/453 SP |
| 3,883,571 | 5/1975 | Allport et al. | 260/453 AM |
| 4,014,935 | 3/1977 | Ibbotson | 260/566 R |
| 4,031,026 | 6/1977 | Ibbotson | 252/182 |
| 4,055,548 | 10/1977 | Carleton et al. | 260/77.5 AT |
| 4,088,665 | 5/1978 | Findeisen et al. | 260/453 AM |
| 4,102,833 | 7/1978 | Salisbury | 521/159 |
| 4,115,429 | 9/1978 | Reiff et al. | 260/453 SP |
| 4,118,411 | 10/1978 | Reiff et al. | 260/453 SP |
| 4,154,752 | 5/1979 | Sundermann et al. | 260/453 SP |
| 4,177,205 | 12/1979 | Schaaf et al. | 260/453 AM |
| 4,229,347 | 10/1980 | Holt et al. | 260/239 A |
| 4,261,852 | 4/1981 | Carroll et al. | 528/59 |
| 4,321,333 | 3/1982 | Alberino et al. | 521/159 |
| 4,332,742 | 6/1982 | Allen | 260/453 SP |

Primary Examiner—Alan Siegel
Attorney, Agent, or Firm—Gene Harsh; Joseph C. Gil

[57] ABSTRACT

The invention is directed to a process for the production of an isocyanate which is both stable and liquid at room temperature comprising reacting pure diphenylmethane diisocyanate or crude diphenylmethane diisocyanate with a diol of the formula,

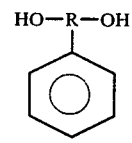

wherein R is a $C_2$ to a $C_5$ aliphatic radical, at a temperature of from 20° to 110° C., in a ratio such that the resultant product has an isocyanate group content of from 20 to 30%, by weight and to the products produced therefrom.

9 Claims, No Drawings

LIQUID DIPHENYLMETHANE DIISOCYANATE COMPOSITIONS

This invention relates to organic isocyanates and mixtures of organic isocyanates based on diphenylmethane diisocyanates which are liquid at room temperature. The invention also relates to a process for preparing these isocyanates.

BACKGROUND OF THE INVENTION

Diisocyanates which are liquid at room temperature have numerous advantages over solid diisocyanates. Diisocyanates which are liquid at room temperature, such as toluene diisocyanate or hexamethylene diisocyanate, are, as a rule, physiologically harmful because of their high vapor pressure. For this reason, various attempts have been made to start with diisocyanates that are solid at room temperature and convert these into the liquid form.

The most commercially important diisocyanates which are solid at room temperature are 4,4'-diphenylmethane diisocyanate and the 2,4'-isomer thereof, which melt at 39° C. and 34.5° C., respectively.

Numerous patents have issued relating to the liquification of diphenylmethane diisocyanate. See, for example, U.S. Pat. Nos. 3,152,162; 3,384,653; 3,394,165; 3,449,256; 3,640,966; 3,641,093; 3,674,828; 3,701,796; 3,883,571; 4,014,935; 4,055,548; 4,088,665; 4,031,026; 4,102,833; 4,115,429; 4,118,411; 4,154,752; 4,177,205; 4,229,347; 4,261,852; 4,321,333; and 4,332,742.

It is an object of this invention to provide improved organic isocyanates which are liquid at room temperature. A further object of this invention is to provide organic isocyanates which remain liquid even on prolonged storage at low temperatures. Still another object of this invention is to provide an improved process for preparing liquid organic isocyanates.

DESCRIPTION OF THE INVENTION

The instant invention is directed to a process for preparing liquid modified isocyanates comprising reacting pure diphenylmethane diisocyanate or crude diphenylmethane diisocyanate with a diol of the formula:

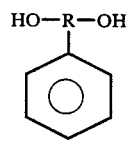

where R is a $C_2$-$C_5$ aliphatic radical (preferably

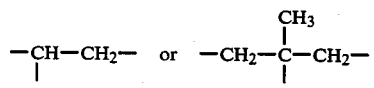

at a temperature between about 20° and about 110° C., preferably between 40° and 80° C., and most preferably between 50° and 70° C., in a ratio such that the product has an isocyanate group content of from 20 to 30 percent, by weight, and preferably of from 22 to 28 percent, by weight. In general, the weight ratio of isocyanate to diol will be from 5:1 to 15:1 and preferably from 6:1 to 13:1. The liquid modified isocyanate may also be prepared as a concentrate (that is, with a lower percent isocyanate group content) and diluted with additional isocyanate to adjust the isocyanate content to the desired level. The instant invention is also directed to isocyanates which are both stable and liquid at room temperature, prepared according to the abovenoted process.

As used herein, the phrase "pure diphenylmethane diisocyanate" means 2,2'-diphenylmethane diisocyanate, 2,4'-diphenylmethane diisocyanate, 4,4'-diphenylmethane diisocyanate and mixtures thereof. The phrase is also intended to include a mixture of one or more of the isomers noted with up to 5 percent, by weight, of a tri- and/or higher isocyanate of the diphenyl type.

As used herein, the phrase "crude diphenylmethane diisocyanate" means an isocyanate mixture which is either (i) a phosgenation product of an undistilled bottom fraction of the type formed during the removal of from 10 to 95%, by weight, of diphenylmethane diamine from an aniline/formaldehyde condensate, or (ii) an undistilled bottom fraction of the type obtained during the removal of from 10 to 95%, by weight, of diphenylmethane diisocyanate from the crude phosgenation product of an aniline/formaldehyde condensate, wherein the isocyanate mixture (a) contains from 25 to 95%, by weight, of diphenylmethane diisocyanate, of which from 1 to 50%, by weight, is the 2,4'-isomer and from 0 to 10%, by weight, is the 2,2'-isomer and the balance is the 4,4'-isomer, (b) has a viscosity of from 10 to 600 cps at 50° C., and (c) has an isocyanate group content of from about 28 to about 33%, by weight.

The liquid isocyanates which can be prepared according to the invention have a very low viscosity and can therefore be processed very easily, such as by casting or metering through pumps. Additionally, they have a very low vapor pressure and are, therefore, less physiologically harmful.

In general, the process may be carried out by introducing the diol into the isocyanate at temperatures from 20° to 110° C., with stirring. The isocyanate content of the product of the process amounts to from 20 to 30 percent, by weight, and preferably to from 22 to 28 percent by weight.

The product of the present invention can be used for many different polyaddition reactions in the lacquer and plastics industry. For example, they may be used in the production of polyurethane foams and elastomers, such as in reaction injection molding (RIM) products.

The invention is further illustrated, but is not intended to be limited by the following examples in which all parts and percentages are by weight unless otherwise specified.

EXAMPLES

EXAMPLE 1

83 parts by weight of 2-methyl-2-phenyl-1,3-propanediol was added over a period of 20 minutes to 625 parts by weight of pure diphenylmethane diisocyanate containing 98 percent, by weight, of the 4,4'-isomer and 2 percent, by weight of the 2,4'-isomer, which had been heated to 50° C. After the reaction mixture was stirred for four hours at 65°–70° C., a liquid, stable product resulted, which had an isocyanate group content of 23.5% and a viscosity of 940 cps at 25° C.

EXAMPLE 2

83 parts by weight of 2-methyl-2-phenyl-1,3-propanediol was added over a period of 10 minutes to 625 parts by weight of pure diphenylmethane diisocyanate containing 35 percent, by weight, of the 4,4'-isomer, 64 percent, by weight, of the 2,4'-isomer, and 1 percent by weight, of the 2,2'-isomer, which had been heated to 30° C. After the reaction mixture was stirred for five hours at 60°–68° C., a liquid, stable product resulted, which had an isocyanate group content of 23.5% and a viscosity of 1,400 cps at 25° C.

EXAMPLE 3

111 parts by weight of phenyl-1,2-ethanediol was added over a period of about 45 minutes, to 900 parts by weight of 4,4'-diphenylmethane diisocyanate which had been heated to 60° C. After the reaction mixture was stirred for one-and-one-half hours, at 60°–65° C., a liquid, stable product resulted which had an isocyanate group content of 23%.

EXAMPLE 4

37 parts by weight of phenyl-1,2-ethanediol was gradually added to 300 parts by weight of 4,4'-diphenylmethane diisocyanate, which had been heated to 60° C. After the reaction mixture was stirred for three hours, at 60°–75° C., a liquid, stable product resulted which had an isocyanate group content of 23%.

EXAMPLE 5

69 parts by weight of phenyl-1,2-ethanediol was added over a period of 15 minutes to 1,035 parts by weight of "crude diphenylmethane diisocyanate" having an isocyanate group content of 33.4 percent, by weight, and a viscosity of 15 cps at 50° C. and containing 95 percent diphenylmethane diisocyanate, of which about 98% is the 4,4'-isomer, and about 2% is the 2,4'-isomer, which had been heated to 50° C. After the reaction mixture was stirred for two hours at 65°–75° C., a liquid, stable product resulted, which had an isocyanate group content of 27.4% and a viscosity of 23.8 cps at 25° C.

EXAMPLE 6

69 parts by weight of phenyl-1,2-ethanediol was added over a period of 15 minutes to 1,035 parts by weight of "crude diphenylmethane diisocyanate" having an isocyanate group content of 33.2%, a viscosity of 20 cps at 50° C., and containing 91 percent diphenylmethane diisocyanate, of which about 94% is the 4,4'-isomer, about 5% is the 2,4'-isomer, and about 1% is the 2,2'-isomer, which had been heated to 50° C. After the reaction mixture was stirred for two hours at 65°–75° C., a liquid, stable product resulted, which had an isocyanate group content of 27.2% and a viscosity of 236 cps at 25° C.

EXAMPLE 7

69 parts by weight of phenyl-1,2-ethanediol was added over a period of 15 minutes to 1,035 parts by weight of "crude diphenylmethane diisocyanate" having an isocyanate group content of 32.6%, a viscosity of 35 cps at 50° C. and containing 75 percent diphenylmethane diisocyanate, of which about 97% is the 4,4'-isomer, and about 3% is the 2,4'-isomer, which had been heated to 50° C. After the reaction mixture was stirred for two hours at 65°–75° C., a liquid, stable product resulted, which had an isocyanate group content of 26.8% and a viscosity of 992 cps at 25° C.

EXAMPLE 8

69 parts by weight of phenyl-1,2-ethanediol was added over a period of 15 minutes to 1,035 parts by weight of "crude diphenylmethane diisocyanate" having an isocyanate group content of 31.6%, a viscosity of 50 cps at 50° C. and containing 55 percent diphenylmethane diisocyanate, of which about 69% is the 4,4'-isomer, about 27% is the 2,4'-isomer and 4% is the 2,2'-isomer, which had been heated to 50° C. After the reaction mixture was stirred for two hours at 65°–75° C., a liquid, stable product resulted, which had an isocyanate group content of 25.8%.

EXAMPLE 9

69 parts by weight of phenyl-1,2-ethanediol was added over a period of 15 minutes to 1,035 parts by weight of "crude diphenylmethane diisocyanate" having an isocyanate group content of 31.6%, a viscosity of 60 cps at 50° C., and containing 50 percent diphenylmethane diisocyanate, of which 96% is the 4,4'-isomer, and 4% is the 2,4'-isomer, which had been heated to 50° C. After the reaction mixture was stirred for two hours at 65°–75° C., a liquid, stable product resulted, which had an isocyanate group content of 25.8%.

What is claimed is:

1. A process for the production of an isocyanate which is both stable and liquid at room temperature comprising reacting pure diphenylmethane diisocyanate or crude diphenylmethane diisocyanate with a diol of the formula,

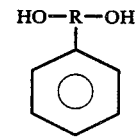

wherein R ia a $C_2$ to $C_5$ aliphatic radical, at a temperature of from 20° to 110° C., in a ratio such that the resultant product has an isocyanate group content of from 20 to 30%, by weight.

2. A process according to claim 1, wherein R is

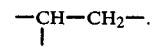

3. A process according to claim 1, wherein R is

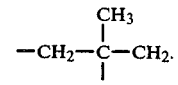

4. The process of claim 1, wherein the temperature is from 40° to 80° C.

5. The process of claim 4, wherein the temperature is from 50° to 70° C.

6. The process of claim 1, wherein the weight ratio of isocyanate to diol is from 5:1 to 15:1.

7. The process of claim 1, wherein the product has an isocyanate group content of from 22 to 28 percent by weight.

8. An isocyanate prepared by reacting pure diphenylmethane diisocyanate or crude diphenylmethane diisocyanate with a diol of the formula,

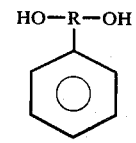

wherein R is a $C_2$ to $C_5$ aliphatic radical, at a temperature of from 20° to 110° C., in a ratio such that the resultant product has an isocyanate group content of from 20 to 30%, by weight.

9. The product of claim 8 having an isocyanate group content of from 22 to 28 percent by weight.

* * * * *